US008604026B2

(12) United States Patent
Gewehr et al.

(10) Patent No.: US 8,604,026 B2
(45) Date of Patent: Dec. 10, 2013

(54) USE OF KIRALAXYL FOR PROTECTING PHYTOPATHOGENS, AND CORRESPONDING METHODS AND COMPOSITIONS

(75) Inventors: Markus Gewehr, Kastellaun (DE); Jan Willem Burgers, Neustadt (DE); Ronald Wilhelm, Hofheim (DE)

(73) Assignee: Isagro S.p.A., Milan (IT)

( * ) Notice: Subject to any disclaimer, the term of this patent is extended or adjusted under 35 U.S.C. 154(b) by 1032 days.

(21) Appl. No.: 12/066,818

(22) PCT Filed: Sep. 12, 2006

(86) PCT No.: PCT/EP2006/008887

§ 371 (c)(1),
(2), (4) Date: Mar. 13, 2008

(87) PCT Pub. No.: WO2007/031283

PCT Pub. Date: Mar. 22, 2007

(65) Prior Publication Data

US 2008/0293707 A1 Nov. 27, 2008

(30) Foreign Application Priority Data

Sep. 13, 2005 (DE) ........................ 10 2005 043 652

(51) Int. Cl.
*A61K 31/535* (2006.01)
*A61K 31/24* (2006.01)
*A01N 37/12* (2006.01)
*A01N 37/44* (2006.01)

(52) U.S. Cl.
USPC ........................................ 514/229.2; 514/537

(58) Field of Classification Search
USPC ............................................... 514/229.2, 537
See application file for complete search history.

(56) References Cited

U.S. PATENT DOCUMENTS

| | | | | | |
|---|---|---|---|---|---|
| 4,849,219 | A * | 7/1989 | Staub et al. | ................... | 424/605 |
| 5,290,791 | A | 3/1994 | Greiner et al. | | |
| 6,011,065 | A | 1/2000 | Young et al. | | |
| 6,228,885 | B1 | 5/2001 | Palla et al. | | |
| 2004/0241098 | A1 * | 12/2004 | Labourdette et al. | ........... | 424/40 |
| 2005/0209304 | A1 * | 9/2005 | Hofer et al. | ................... | 514/422 |

FOREIGN PATENT DOCUMENTS

| | | | | | |
|---|---|---|---|---|---|
| EP | 0253714 | A | 1/1988 | | |
| EP | 0935917 | A1 | 8/1999 | | |
| EP | 1023832 | * | 1/2000 | ............. | A01N 25/04 |
| GB | 2213063 | A | 8/1989 | | |
| GB | 2213727 | A | 8/1989 | | |
| WO | WO97/22254 | * | 6/1997 | ............. | A01N 43/88 |
| WO | WO-98/26654 | A | 6/1998 | | |
| WO | WO-2004/080181 | A | 9/2004 | | |
| WO | WO-2006/023899 | A | 3/2006 | | |
| WO | WO-2006/040123 | A | 4/2006 | | |
| WO | WO-2006/066810 | A | 6/2006 | | |
| WO | WO-2006/131246 | A | 12/2006 | | |

* cited by examiner

*Primary Examiner* — Sean Basquill
(74) *Attorney, Agent, or Firm* — Birch, Stewart, Kolasch & Birch, LLP

(57) ABSTRACT

The invention relates to a method for protecting against phytopathogens which comprises treating seed with kiralaxyl (methyl N-(phenylacetyl)-N-(2,6-xylyl)-D-alaninate) in combination with at least one further pesticide and furthermore to the corresponding use of kiralaxyl in combination with at least one further pesticide and to corresponding compositions. Also described is special seed.

10 Claims, No Drawings

USE OF KIRALAXYL FOR PROTECTING PHYTOPATHOGENS, AND CORRESPONDING METHODS AND COMPOSITIONS

The present invention relates to a method for protecting against phytopathogens which comprises the application of kiralaxyl (methyl N-(phenylacetyl)-N-(2,6-xylyl)-D-alaninate) in combination with at least one further pesticide, furthermore to the corresponding use of kiralaxyl in combination with at least one further pesticide and to corresponding compositions.

Before and during germination and emergence, plants tend to be particularly sensitive toward harmful organisms, not only because the small size of the developing plant organs makes it impossible for them to overcome relatively large damage, but also because some of the natural defense mechanisms of the plants in this development phase are not yet developed. Accordingly, for reducing damage by foreign organisms it is of essential importance to protect the plants before and immediately after germination.

It is of particular importance that damage by an organism, as a result of the break-down of natural barriers (for example the plant surface) and/or general damage of the plants may predispose the plant to secondary damage by abiotic factors (for example easier breaking of plants at high wind as a result of insect feeding damage) and also to other pests (for example facilitating fungal infections where insect feeding damage is present). Here, the secondary damage may be much worse than the primary damage.

Pesticides are substances which are capable of controlling individual types of harmful organisms with high specificity; depending on the specificity, the pesticides are classified as insecticides, acaricides, vermicides/nematicides, molluscicides, fungicides, etc., the possible mechanisms including repelling, killing, hindering the reproduction, etc., of harmful organisms. There is a desire for the specificity to be as high as possible so that neither useful organisms nor the user are damaged by the pesticide application; it goes without saying that the price for this specificity is a correspondingly narrowly defined spectrum of action and that as a consequence pesticides are generally not capable of preventing secondary damage by other organisms.

However, the customary application of pesticides to plants and their habitats, hereinbelow referred to as field application, has a number of possible disadvantages: in many cases, resistance to a given pesticide develops fast, namely when the application is to large areas, so that there is a constant need for the development of novel pesticides. The possible negative effects of pesticides on environment and human health have attracted the attention of the public. In particular for people employed in agriculture, a generous use of pesticides is a serious health risk. Accordingly, it is recommended to work with dosages which are as low as possible. A successful defense against harmful organisms requires good coordination and a high work input and may, depending on the formulation used, be highly sensitive to abiotic factors such as wind, temperature and rain, which are difficult to control. Moreover, there is always the undesired possibility that, owing to diffusion and convection, pesticides may not remain at the site of application, which has the additional disadvantage that not only useful plants but also weeds are protected.

Accordingly, ideally, the pesticide should be effective at comparatively low dosages, should not be subject to large-scale diffusion into the environment and away from the plants to be treated (which would lead to unwanted bystander effects) and should be suitable for methods where both human exposure and work input are reduced. Furthermore, it should be possible to provide, by a uniform treatment method, simultaneous protection against a plurality of the most important harmful organisms of the same or different taxonomic groups, in order to prevent secondary damage in this manner.

Methyl N-(phenylacetyl)-N-(2,6-xylyl)-D-alaninate (according to the CIP nomenclature methyl N-(phenylacetyl)-N-(2,6-xylyl)-R-alaninate), also known under the name kiralaxyl, is a highly effective fungicide. WO 98/26654, for example, describes mixtures of methyl N-(phenylacetyl)-N-(2,6-xylyl)alaninate and at least one other fungicide for treating fungal infections, in particular oomycetes infections (genera *Plasmopara, Phytophthora, Peronospora, Pseudoperonospora* and *Pythium*), on useful plants by applying the mixtures to plants at risk or plants already infected, and/or their habitat. Here, the methyl N-(phenylacetyl)-N-(2,6-xylyl)alaninate should comprise more than 50% of the levorotatory enantiomorph.

It is an object of the present invention to develop novel methods for using kiralaxyl which allow the disadvantages of field application to be avoided and which, at the same time, provide combined protection against harmful organisms which may damage the plants particularly severely either together with fungal diseases or subsequently thereto.

Surprisingly, it has been found that this object is achieved by treating seeds of the plants to be protected with kiralaxyl in combination with further fungicides and/or insecticides.

Accordingly, the invention provides a method for protecting a plant against a phytopathogen selected from the genera *Pythium, Rhizoctonia, Tilletia, Ustilago, Peronospora, Pseudoperonospora, Plasmopara, Alternaria, Cercospora, Drechslera, Fusarium* and *Verticillium*, wherein the seed of the plant is treated with A) kiralaxyl of the formula I (I)

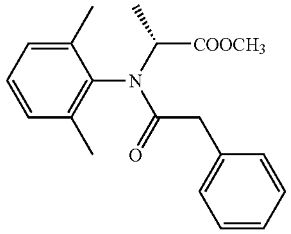

in combination with at least one further pesticide selected from

B) further fungicides and

C) insecticides.

The invention also provides the use of

A) kiralaxyl of the formula I (I)

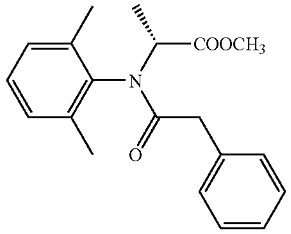

in combination with at least one further pesticide selected from

B) further fungicides and

C) insecticides, for treating seed of a plant for protecting the plant against a phytopathogen selected from the genera *Pythium, Rhizoctonia, Tilletia, Ustilago, Peronospora, Pseudoperonospora, Plasmopara, Alternaria, Cercospora, Drechslera, Fusarium* and *Verticillium.*

The invention also provides a composition for treating seed of a plant for protecting the plant against a phytopathogen selected from the genera *Pythium, Rhizoctonia, Tilletia, Ustilago, Peronospora, Pseudoperonospora, Plasmopara, Alternaria, Cercospora, Drechslera, Fusarium* and *Verticillium*, the composition comprising:

A) kiralaxyl of the formula I (I)

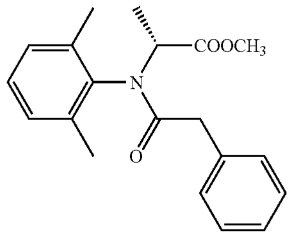

in combination with at least one further pesticide selected from

B) further fungicides and

C) insecticides.

The invention also provides seed comprising

A) kiralaxyl of the formula I (I)

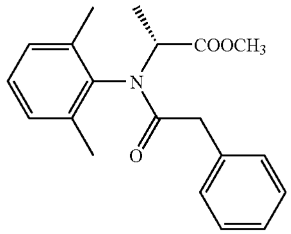

in combination with at least one further pesticide selected from

B) further fungicides and

C) insecticides.

The invention also provides seed obtainable by a method according to the invention.

Kiralaxyl (component A) is a known fungicide from the group of the acylalanines and represents essentially enantiomerically pure methyl N-(phenylacetyl)-N-(2,6-xylyl)-D-alaninate of the formula I. This does not preclude that the kiralaxyl-comprising preparation, for example a process product or commercial product, may also comprise small amounts of methyl N-(phenylacetyl)-N-(2,6-xylyl)-L-alaninate. However, according to the invention such proportions are relatively low. In this sense, for methods, uses and compositions according to the invention, the weight ratio of methyl N-(phenylacetyl)-N-(2,6-xylyl)-D-alaninate to methyl N-(phenylacetyl)-N-(2,6-xylyl)-L-alaninate is at least 9:1, preferably at least 19:1 and in particular at least 99:1.

Processes for preparing kiralaxyl are known in principle and described, for example, in WO 00/76960, the entire content of which is expressly incorporated herein by way of reference. Alternative processes for synthesizing kiralaxyl are described in WO 98/26654.

The further fungicide may, in principle, be any active compound with fungicidal action. Such compounds are listed, for example, in standard works such as *The Pesticide Manual*, British Crop Protection Council, 13th Edition 2003, the entire content of which is expressly incorporated herein by way of reference. The further fungicide is in particular selected from acylalanines, such as metalaxyl, ofurace, oxadixyl;

amine derivatives, such as aldimorph, dodine, dodemorph, fenpropimorph, fenpropidin, guazatine, iminoctadine, spiroxamine, tridemorph;

anilinopyrimidines, such as pyrimethanil, mepanipyrim or cyprodinyl;

antibiotics, such as cycloheximide, griseofulvin, kasugamycin, natamycin, polyoxin, streptomycin and validamycin A;

azoles, such as bitertanol, bromuconazole, cyazofamid, cyproconazole, difenoconazole, dinitroconazole, epoxiconazole, etridazole, fenbuconazole, fluquinconazole, flusilazole, flutriafol, fuberidazole, hexaconazole, hymexazole, imazalil, ipconazole, imibenconazole, metconazole, myclobutanil, penconazole, perfuazorate, propiconazole, prochloraz, prothioconazole, simeconazole, tebuconazole, tetraconazole, thiabendazole, triadimefon, triadimenol, triflumizole, triticonazole, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

2-methoxybenzophenones as described in EP-A 897904 by the general formula I, for example metrafenone;

dicarboximides, such as iprodione, myclozolin, procymidone, vinclozolin;

dithiocarbamates, such as ferbam, nabam, maneb, mancozeb, metam, metiram, propineb, polycarbamate, thiram, ziram, zineb;

heterocyclic compounds, such as anilazine, benomyl, boscalid, carbendazim, carboxin, oxycarboxin, cyazofamid, dazomet, dithianone, ethirimol, dimethirimol, famoxadone, fenamidone, fenarimol, fuberidazole, flutolanil, furametpyr, isoprothiolane, mepronil, nuarimol, octhilinone, picobezamid, probenazole, proquinazid, pyrifenox, pyroquilon, quinoxyfen, silthiofam, thiabendazole, thifluzamide, thiophanate-methyl, tiadinil, tricyclazole, triforine, 3-[5-(4-chlorophenyl)-2,3-dimethylisoxazolidin-3-yl]pyridine, and bupirimate;

nitrophenyl derivatives, such as binapacryl, dinocap, dinobuton, nitrophthal-isopropyl;

phenylpyrroles, such as fenpiclonil, and also fludioxonil;

further unclassified fungicides, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenone, pencycuron, propamocarb, phthalide, tolclofos-methyl, quintozene, zoxamide, isoprothiolane, fluopicolide (picobenzamid), carpropamid, mandipropamid, N-(2-{4-[3-(4-chlorophenyl)prop-2-ynyloxy]-3-methoxy-phenyl}ethyl)-2-methanesulfonylamino-3-methylbutyramide, N-(2-{4-[3-(4-chlorophenyl)prop-2-ynyloxy]-3-methoxyphenyl}ethyl)-2-ethanesulfonylamino-3-methylbutyramide, furametpyr, thifluzamide, penthiopyrad, fenhexamid, N-(2-cyanophenyl)-3,4- dichloroisothiazole-5-carboxamide, flubenthiavalicarb, methyl 3-(4-chlorophenyl)-3-(2-isopropoxycarbonylamino-3-methylbutyrylamino)-propionate, methyl {2-chloro-5-[1-(6-methylpyridin-2-ylmethoxyimino) ethyl]-benzyl}carbamate, methyl {2-chloro-5-[1-(3-methylbenzyloxyimino)ethyl]-benzyl}carbamate, flusulfamide, amides, described in WO 03/66610 of the formulae

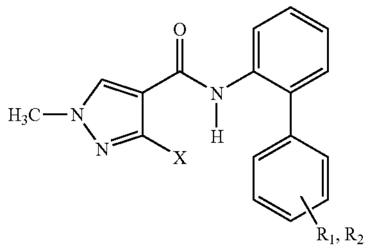

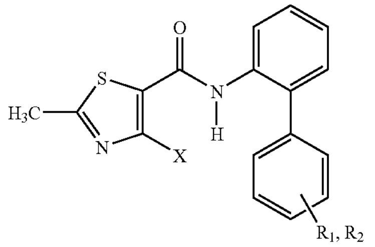

in which

X is $CHF_2$, $CF_3$ or $CH_3$; and $R^1$, $R^2$ independently of one another are halogen, methyl, halomethyl, for example $CF_3$, methoxy, halomethoxy, for example $OCF_3$ or CN, for example N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide or N-(3,4'-dichloro-4-fluorobiphenyl-2-yl)-3-difluoromethyl-1-methylpyrazole-4-carboxamide;

strobilurins as described in WO 03/075663 by the general formula I, for example azoxystrobin, dimoxystrobin, fluoxastrobin, kresoxim-methyl, metominostrobin, orysastrobin, picoxystrobin, pyraclostrobin and trifloxystrobin;

sulfenic acid derivatives, such as captafol, captan, dichlofluanid, folpet, tolyl-fluanid;

cinnamides and analogues, such as dimethomorph, flumetover, flumorp;

6-aryl-[1,2,4]triazolo[1,5-a]pyrimidines, as described, for example, in WO 98/46608, WO 99/41255 or WO 03/004465, in each case by the general formula I, for example 5-chloro-7-(4-methylpiperidin-1-yl)-6-(2,4,6-trifluorophenyl)-[1,2,4]triazolo[1,5-a]pyrimidine;

amide fungicides, such as cyclofenamid and also (Z)—N-[α-(cyclopropyl-methoxyimino)-2,3-difluoro-6-(difluoromethoxy)benzyl]-2-phenylacetamide.

From among these, fungicides from the classes of the anilinopyrimidines, azoles, dicarboximides, heterocyclic compounds, phenylpyrroles, strobilurins, 6-aryl-[1,2,4]triazolo [1,5-a]pyrimidines and cinnamides are especially preferred.

In principle, the insecticide may be any active compound having insecticidal action. Such compounds can be found, for example, in standard works such as *The Pesticide Manual*, British Crop Protection Council, 13th Edition 2003, which is incorporated herein in its entirety by way of reference. In particular, the insecticide is selected from organo(thio)phosphates, such as acephate, azamethiphos, azinphos-methyl, chlorpyrifos, chlorpyrifos-methyl, chlorfenvinphos, diazinon, dichlorphos, dimethylvinphos, dioxabenzofos, dicrotophos, dimethoate, disulfoton, ethion, EPN, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, primiphos-ethyl, pyraclofos, pyridaphenthion, sulprophos, triazophos, trichlorfon; tetrachlorvinphos, vamidothion;

carbamates, such as alanycarb, benfuracarb, bendiocarb, carbaryl, carbofuran, carbosulfan, fenoxycarb, furathiocarb, indoxacarb, methiocarb, methomyl, oxamyl, pirimicarb, propoxur, thiodicarb, triazamate;

pyrethroids, such as allethrin, bifenthrin, cyfluthrin, cyphenothrin, cycloprothrin, cypermethrin, deltamethrin, esfenvalerate, ethofenprox, fenpropathrin, fenvalerate, cyhalothrin, lambda-cyhalothrin, imoprothrin, permethrin, prallethrin, pyrethrin I, pyrethrin II, silafluofen, tau-fluvalinate, tefluthrin, tralomethrin, transfluthrin, alpha-cypermethrin, zeta-cypermethrin, permethrin;

arthropod growth regulators: a) chitin synthesis inhibitors, for example benzoylureas, such as chlorfluazuron, cyromazine, diflubenzuron, flucycloxuron, flufenoxuron, hexaflumuron, lufenuron, novaluron, teflubenzuron, triflumuron, buprofezin, diofenolan, hexythiazox, etoxazole, clofentazine; b) ecdysone antagonists, such as halofenozide, methoxyfenozide, tebufenozide; c) juvenoids, such as pyriproxyfen, methoprene, fenoxycarb; d) lipid biosynthesis inhibitors, such as spirodiclofen;

neonicotinoids, such as flonicamid, clothianidin, dinotefuran, imidacloprid, thiamethoxam, nitenpyram, nithiazine, acetamiprid, thiacloprid;

further unclassified insecticides, such as abamectin, acequinocyl, acetamiprid, amitraz, azadirachtin, bensultap, bifenazate, cartap, chlorfenapyr, chlordimeform, cyromazine, diafenthiuron, dinetofuran, diofenolan, emamectin, endosulfan, ethiprole, fenazaquin, fipronil, formetanate, formetanate hydrochloride, gamma-HCH, hydramethylnon, imidacloprid, indoxacarb, isoprocarb, metolcarb, pyridaben, pymetrozine, spinosad, tebufenpyrad, thiamethoxam, thiocyclam, pyridalyl, flonicamid, fluacypyrim, milbemectin, spiromesifen, flupyrazofos, NC 512, tolfenpyrad, flubendiamide, bistrifluoron, benclothiaz, pyrafluprole, pyriprole, amidoflumet, flufenerim, cyflumetofen, acequinocyl, lepimectin, profluthrin, dimefluthrin, amidrazone, N—R'-2,2-dihalo-1-R''-cyclopropanecarboxamide-2-(2,6-dichloro-α,α,α-trifluoro-p-tolyl)hydrazone, N—R'-2,2-di(R''')propionamide-2-(2,6-dichloro-α,α,α-trifluoro-p-tolyl)-hydrazone, where halo is chlorine or bromine, R' is methyl or ethyl, R'' is hydrogen or methyl and R''' is methyl or ethyl, XMC and xylylcarb and also the compound of the formula below

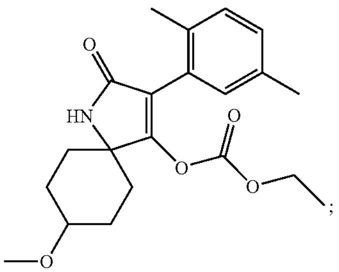 [SMILES: CCOC(=O)OC1=C(c2cc(C)ccc2C)C(=O)NC12CCC(OC)CC2 ; ";"]

aminoisothiazoles of the formula

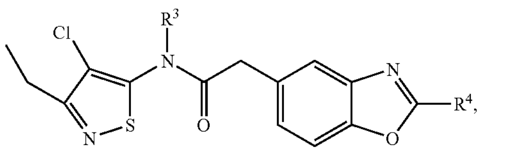

in which $R^3$=—$CH_2OCH_3$ or H and $R^4$=—$CF_2CF_2CF_3$;

anthranilamides of the formula

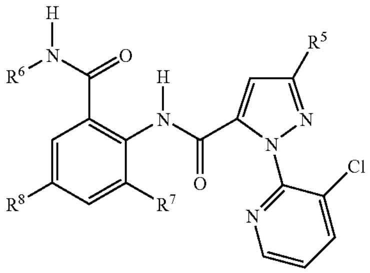

in which $R^5$=Br, $CF_3$, $OC_1$-$C_4$-alkyl;

$R^6$=$C_1$-$C_4$-alkyl;

$R^7$=Cl, methyl, $R^8$=Cl, CN, for example anthranilamides of the formula

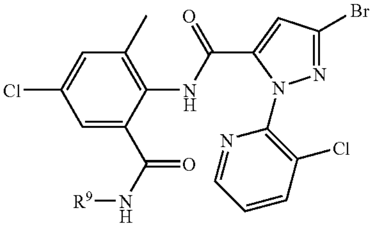

in which $R^9$=$C_1$-$C_4$-alkyl;

and also the compound of the formula below

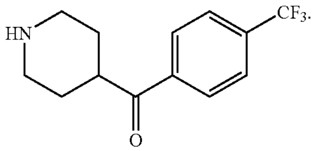 [SMILES: O=C(c1ccc(C(F)(F)F)cc1)C1CCNCC1]

From among these, insecticides from the classes of the pyrethroids, neonicotinoids and unclassified insecticides are especially preferred.

Some of the fungicides of component B and the insecticides of component C are known pesticides, and processes for their preparation are known from the prior art.

Thus, orysastrobin and processes for its preparation are described, for example, in *Agrow* 399, 26 (2002), the entire content of which is incorporated herein by way of reference.

Triticonazole and processes for its preparation are described, for example, in *Agrow* 166, 24 (1992), the entire content of which is incorporated herein by way of reference.

Boscalid and processes for its preparation are described, for example, in *Agrow* 384, 22 (2001), the entire content of which is incorporated herein by way of reference.

Fluopicolid and processes for its preparation are described, for example, in WO 99/42447, the entire content of which is incorporated herein by way of reference.

The *Crop Protection Handbook*, Volume 89, Meister Publishing, USA 2003, the entire content of which is incorporated herein by way of reference, describes the following fungicides and processes for their preparation: fluoxastrobin (page C 238), prothioconazole (page C 394).

5-Chloro-7-(4-methylpiperidin-1-yl)-6-(2,4,6-trifluorophenyl)-[1,2,4]triazolo[1,5-a]-pyrimidine and processes for its preparation are described, for example, in WO 98/46608.

*The Pesticide Manual,* 13th Edition, British Crop Protection Council 2003 describes the following fungicides or insecticides and processes for their preparation: pyraclostrobin, iprodione, dimethomorph, fluquinconazole, prochloraz, prothioconazole, difenoconazole, tebuconazole, penconazole, propiconazole, azoxystrobin, triazoxide, carboxin, triadimenol, fipronil, imadacloprid, thiamethoxam, acetamiprid, clothianidin, alpha-cypermethrin, tefluthrin, spinosad, thiacloprid, pyrimethanil, fludioxonil.

If the further fungicides of component B) or the insecticides of component C) form geometric isomers, for example E/Z isomers, it is possible to use according to the invention both the pure isomers and mixtures thereof. If these compounds have one or more centers of chirality and may thus be present as enantiomers or diastereomers, it is possible to use both the pure enantiomers and the diastereomers and mixtures thereof, for example racemic mixtures, in the compositions according to the invention.

If kiralaxyl, the further fungicides of component B) and the insecticides of component C) have ionizable functional groups, they can also be employed in the form of their agriculturally compatible salts. Thus, if, for example, they have basic functional groups, they can be employed in the form of their acid addition salts. Suitable are, in general, the acid addition salts of those acids whose anions have no adverse effect on the action of the active compounds.

Anions of useful acid addition salts are primarily chloride, bromide, fluoride, iodide, sulfate, hydrogensulfate, methyl sulfate, phosphate, hydrogenphosphate, dihydrogen-phosphate, nitrate, carbonate, bicarbonate, hexafluorosilicate, hexafluorophosphate, benzoate, and also the anions of $C_1$-$C_4$-alkanoic acids, preferably formate, acetate, propionate and butyrate.

The following active compounds, for example, can be used in the form of acid addition salts: pyraclostrobin, prochloraz, triticonazole, tebuconazole and spinosad.

According to a particular embodiment, the further pesticide is selected from the group consisting of triticonazole, orysastrobin, pyraclostrobin, boscalid, 5-chloro-7-(4-methylpiperidin-1-yl)-6-(2,4,6-trifluorophenyl)-[1,2,4]triazolo[1,5-a]pyrimidine, iprodione, pyrimethanil, dimethomorph, fluquinconazole, prochloraz, metconazole, prothioconazole, difenoconazole, tebuconazole, penconazole, propiconazole, fluoxastrobin, azoxystrobin, triazoxide, carboxin, fludioxonil, triadimenol, fipronil, imidacloprid, thiamethoxam, acetamiprid, clothianidin, alpha-cypermethrin, tefluthrin, spinosad and thiacloprid. From among these, preference is given to triticonazole, orysastrobin, pyraclostrobin, boscalid, 5-chloro-7-(4-methylpiperidin-1-yl)-6-(2,4,6-trifluorophenyl)-[1,2,4]triazolo[1,5-a]pyrimidine, iprodione, pyrimethanil, fluquinconazole, prochloraz, metconazole, fipronil, imidacloprid, thiamethoxam, acetamiprid, clothianidin and alpha-cypermethrin. In the context of this embodiment, combinations of kiralaxyl with 1, 2, 3, 4 or 5 of these further pesticides are of particular interest.

According to a particular embodiment, the further fungicide is selected from the group consisting of triticonazole, orysastrobin, pyraclostrobin, boscalid, 5-chloro-7-(4-methylpiperidin-1-yl)-6-(2,4,6-trifluorophenyl)-[1,2,4]triazolo[1,5-a]pyrimidine, iprodione, pyrimethanil, dimethomorph, fluquinconazole, prochloraz, metconazole, prothioconazole, difenoconazole, tebuconazole, penconazole, propiconazole, fluoxastrobin, azoxystrobin, triazoxide, carboxin, fludioxonil and triadimenol. From among these, preference is given to triticonazole, orysastrobin, pyraclostrobin, boscalid, 5-chloro-7-(4-methylpiperidin-1-yl)-6-(2,4,6-trifluorophenyl)-[1,2,4]triazolo[1,5-a]pyrimidine, iprodione, pyrimethanil, fluquinconazole, prochloraz and metconazole. In the context of this embodiment, combinations of kiralaxyl with 1, 2 or 3 of these further fungicides are of particular interest.

According to a further particular embodiment, the further fungicide is selected from the group consisting of triticonazole, orysastrobin, pyraclostrobin, boscalid, 5-chloro-7-(4-methylpiperidin-1-yl)-6-(2,4,6-trifluorophenyl)-[1,2,4]triazolo[1,5-a]pyrimidine, iprodione, pyrimethanil, fluquinconazole, prochloraz, metconazole, prothioconazole, difenoconazole, tebuconazole, penconazole, fluoxastrobin, triazoxide, carboxin and fludioxonil. From among these, preference is given to orysastrobin, pyraclostrobin, boscalid, 5-chloro-7-(4-methylpiperidin-1-yl)-6-(2,4,6-trifluorophenyl)-[1,2,4]triazolo-[1,5-a]pyrimidine, fluquinconazole, prothioconazole, fluoxastrobin and carboxin, and very particular preference is given to orysastrobin, pyraclostrobin, boscalid, 5-chloro-7-(4-methylpiperidin-1-yl)-6-(2,4,6-trifluorophenyl)-[1,2,4]triazolo[1,5-a]pyrimidine and fluquinconazole. In the context of this embodiment, combinations of kiralaxyl with 1, 2 or 3 of these further fungicides are of particular interest.

According to a further particular embodiment, the insecticide is selected from the group consisting of fipronil, imidacloprid, thiamethoxam, acetamiprid, clothianidin, alpha-cypermethrin, tefluthrin, spinosad, thiacloprid. From among these, preference is given to fipronil, imidacloprid, thiamethoxam, acetamiprid, clothianidin and alpha-cypermethrin. In the context of this embodiment, combinations of kiralaxyl with 1, 2 or 3 of these insecticides are of particular interest.

According to a particular embodiment, at least one combination partner of the kiralaxyl is selected from insecticides, in particular those mentioned above.

According to the invention, kiralaxyl and the additional pesticide can be used as binary, ternary, quaternary, quinternary or higher combinations.

In the context of the present invention, binary combinations are to be understood as meaning combinations in which, in addition to kiralaxyl, only one further fungicide or insecticide is used as fungicidally or insecticidally active compound. Correspondingly, ternary combinations are combinations in which, in addition to kiralaxyl, two different further fungicides, two different insecticides or one further fungicide and one insecticide are used as fungicidally or insecticidally active compounds. Correspondingly, quaternary combinations are combinations in which, in addition to kiralaxyl, three different further fungicides, three different insecticides, two different further fungicides and one insecticide or one further fungicide and two different insecticides are used as fungicidally or insecticidally active compounds. Correspondingly, quinternary combinations include combinations in which, in addition to kiralaxyl, three different further fungicides and one insecticide, two different further fungicides and two different insecticides or one further fungicide and three different insecticides are used as fungicidally or insecticidally active compounds.

According to the invention, kiralaxyl and the further pesticide(s) selected from further fungicides and insecticides (i.e. the component B and/or the component C) are preferably employed in a weight ratio such that their combined application results in advantages, for example a synergistic action. In general, the weight ratio of kiralaxyl to the further pesticide (or the further pesticides) is from 200:1 to 1:200, more preferably from 100:1 to 1:100, particularly preferably from 50:1 to 1:50 and especially from 10:1 to 1:10. In the case of ternary and higher combinations, the weight ratio of the further pesticides among one another is preferably from 100:1 to 1:100, particularly preferably from 50:1 to 1:50 and especially from 10:1 to 1:10.

Examples of binary combinations of kiralaxyl and a further fungicide B are listed in table 1a below.

TABLE 1a

Binary combinations of kiralaxyl and a further fungicide B

| Combination | Further fungicide B | Weight ratio kiralaxyl:fungicide B |
|---|---|---|
| 1. | triticonazole | 100:1 to 1:100, particularly preferably 50:1 to 1:50, especially 10:1 to 1:10 |
| 2. | orysastrobin | 100:1 to 1:100, particularly preferably 50:1 to 1:50, especially 10:1 to 1:10 |
| 3. | pyraclostrobin | 100:1 to 1:100, particularly preferably 50:1 to 1:50, especially 10:1 to 1:10 |
| 4. | boscalid | 100:1 to 1:100, particularly preferably 50:1 to 1:50, especially 10:1 to 1:10 |
| 5. | 5-chloro-7-(4-methylpiperidin-1-yl)-6-(2,4,6-trifluorophenyl)-[1,2,4]triazolo[1,5-a]pyrimidine | 100:1 to 1:100, particularly preferably 50:1 to 1:50, especially 10:1 to 1:10 |
| 6. | iprodione | 100:1 to 1:100, particularly preferably 50:1 to 1:50, especially 10:1 to 1:10 |
| 7. | pyrimethanil | 100:1 to 1:100, particularly preferably 50:1 to 1:50, especially 10:1 to 1:10 |
| 8 | dimethomorph | 100:1 to 1:100, particularly preferably 50:1 to 1:50, especially 10:1 to 1:10 |
| 9. | fluquinconazole | 100:1 to 1:100, particularly preferably 50:1 to 1:50, especially 10:1 to 1:10 |

TABLE 1a-continued

| Binary combinations of kiralaxyl and a further fungicide B | | |
|---|---|---|
| Combination | Further fungicide B | Weight ratio kiralaxyl:fungicide B |
| 10. | prochloraz | 100:1 to 1:100, particularly preferably 50:1 to 1:50, especially 10:1 to 1:10 |
| 11. | metconazole | 100:1 to 1:100, particularly preferably 50:1 to 1:50, especially 10:1 to 1:10 |
| 12. | prothioconazole | 100:1 to 1:100, particularly preferably 50:1 to 1:50, especially 10:1 to 1:10 |
| 13. | difenoconazole | 100:1 to 1:100, particularly preferably 50:1 to 1:50, especially 10:1 to 1:10 |
| 14. | tebuconazole | 100:1 to 1:100, particularly preferably 50:1 to 1:50, especially 10:1 to 1:10 |
| 15. | penconazole | 100:1 to 1:100, particularly preferably 50:1 to 1:50, especially 10:1 to 1:10 |
| 16. | propiconazole | 100:1 to 1:100, particularly preferably 50:1 to 1:50, especially 10:1 to 1:10 |
| 17. | fluoxastrobin | 100:1 to 1:100, particularly preferably 50:1 to 1:50, especially 10:1 to 1:10 |
| 18. | azoxystrobin | 100:1 to 1:100, particularly preferably 50:1 to 1:50, especially 10:1 to 1:10 |
| 19. | triazoxide | 100:1 to 1:100, particularly preferably 50:1 to 1:50, especially 10:1 to 1:10 |
| 20. | carboxin | 100:1 to 1:100, particularly preferably 50:1 to 1:50, especially 10:1 to 1:10 |
| 21. | fludioxonil | 100:1 to 1:100, particularly preferably 50:1 to 1:50, especially 10:1 to 1:10 |
| 22. | triadimenol | 100:1 to 1:100, particularly preferably 50:1 to 1:50, especially 10:1 to 1:10 |

Examples of binary combinations of kiralaxyl and a further insecticide C are listed in table 1b.

TABLE 1b

| Binary combinations of kiralaxyl and an insecticide C | | |
|---|---|---|
| Combination | Insecticide C | Weight ratio kiralaxyl:insecticide C |
| 23. | fipronil | 100:1 to 1:100, particularly preferably 50:1 to 1:50, especially 10:1 to 1:10 |
| 24. | imidacloprid | 100:1 to 1:100, particularly preferably 50:1 to 1:50, especially 10:1 to 1:10 |
| 25. | thiamethoxam | 100:1 to 1:100, particularly preferably 50:1 to 1:50, especially 10:1 to 1:10 |
| 26. | acetamiprid | 100:1 to 1:100, particularly preferably 50:1 to 1:50, especially 10:1 to 1:10 |
| 27. | clothianidin | 100:1 to 1:100, particularly preferably 50:1 to 1:50, especially 10:1 to 1:10 |
| 28. | alpha-cypermethrin | 100:1 to 1:100, particularly preferably 50:1 to 1:50, especially 10:1 to 1:10 |
| 29. | tefluthrin | 100:1 to 1:100, particularly preferably 50:1 to 1:50, especially 10:1 to 1:10 |
| 30. | spinosad | 100:1 to 1:100, particularly preferably 50:1 to 1:50, especially 10:1 to 1:10 |
| 31. | thiacloprid | 100:1 to 1:100, particularly preferably 50:1 to 1:50, especially 10:1 to 1:10 |

Examples of ternary combinations of kiralaxyl and two further fungicides B1 and B2 are listed in table 2a.

TABLE 2a

| Ternary combinations of kiralaxyl and two further fungicides B1 and B2 | | | |
|---|---|---|---|
| Combination | Further fungicide B1 | Further fungicide B2 | Weight ratio kiralaxyl:(fungicide B1 + B2) |
| 32. | triticonazole | pyraclostrobin | 100:1 to 1:100, particularly preferably 50:1 to 1:50, especially 10:1 to 1:10 |
| 33. | triticonazole | 5-chloro-7-(4-methylpiperidin-1-yl)-6-(2,4,6-trifluorophenyl)-[1,2,4]triazolo[1,5-a]pyrimidine | 100:1 to 1:100, particularly preferably 50:1 to 1:50, especially 10:1 to 1:10 |
| 34. | triticonazole | prochloraz | 100:1 to 1:100, particularly preferably 50:1 to 1:50, especially 10:1 to 1:10 |
| 35. | pyraclostrobin | boscalid | 100:1 to 1:100, particularly preferably 50:1 to 1:50, especially 10:1 to 1:10 |
| 36. | pyraclostrobin | dimethomorph | 100:1 to 1:100, particularly preferably 50:1 to 1:50, especially 10:1 to 1:10 |
| 37. | pyraclostrobin | thiophanate-methyl | 100:1 to 1:100, particularly preferably 50:1 to 1:50, especially 10:1 to 1:10 |
| 38. | boscalid | metconazole | 100:1 to 1:100, particularly preferably 50:1 to 1:50, especially 10:1 to 1:10 |
| 39. | boscalid | 5-chloro-7-(4-methylpiperidin-1-yl)-6-(2,4,6-trifluorophenyl)-[1,2,4]triazolo[1,5-a]pyrimidine | 100:1 to 1:100, particularly preferably 50:1 to 1:50, especially 10:1 to 1:10 |
| 40. | boscalid | orysastrobin | 100:1 to 1:100, particularly preferably 50:1 to 1:50, especially 10:1 to 1:10 |
| 41. | fluquinconazole | prochloraz | 100:1 to 1:100, particularly preferably 50:1 to 1:50, especially 10:1 to 1:10 |

Examples of ternary combinations of kiralaxyl and two insecticides C1 and C2 are listed in table 2b.

TABLE 2b

Ternary combinations of kiralaxyl and two insecticides C1 and C2

| Combination | Insecticide C1 | Insecticide C2 | Weight ratio kiralaxyl:(insecticide C1 + C2) |
|---|---|---|---|
| 42. | fipronil | alpha-cypermethrin | 100:1 to 1:100, particularly preferably 50:1 to 1:50, especially 10:1 to 1:10 |
| 43. | fipronil | imidacloprid | 100:1 to 1:100, particularly preferably 50:1 to 1:50, especially 10:1 to 1:10 |
| 44. | fipronil | thiamethoxam | 100:1 to 1:100, particularly preferably 50:1 to 1:50, especially 10:1 to 1:10 |
| 45. | fipronil | acetamiprid | 100:1 to 1:100, particularly preferably 50:1 to 1:50, especially 10:1 to 1:10 |
| 46. | alpha-cypermethrin | acetamiprid | 100:1 to 1:100, particularly preferably 50:1 to 1:50, especially 10:1 to 1:10 |

Examples of preferred ternary combinations of kiralaxyl, a further fungicide B and an insecticide C result when tables 1a and 1b are viewed together. These are ternary combinations in which each further fungicide B from the combinations 1 to 22 disclosed in table 1a are combined with each insecticide from combinations 23 to 32 disclosed in table 1b.

Examples of preferred quaternary combinations of kiralaxyl and three further fungicides B1, B2 and B3 are listed in table 3.

TABLE 3

Quaternary combinations of kiralaxyl and three further fungicides B1, B2 and B3

| Combination | Fungicide B1 | Fungicide B2 | Fungicide B3 | Weight ratio kiralaxyl:(fungicide B1 + B2 + B3) |
|---|---|---|---|---|
| 47. | pyraclostrobin | boscalid | dimethomorph | 100:1 to 1:100, particularly preferably 50:1 to 1:50, especially 10:1 to 1:10 |

Examples of preferred quaternary combinations of kiralaxyl, two further fungicides B1 and B2 and one insecticide C result when tables 2a and 1b are viewed together. These are quaternary combinations in which each combination of the further fungicides B1 and B2 of the combinations 32 to 41 disclosed in table 2a is combined with each insecticide from the combinations 23 to 31 disclosed in table 1b.

Examples of preferred quaternary combinations of kiralaxyl, a further fungicide B and two insecticides C1 and C2 result when tables 1a and 2b are viewed together. These are quaternary combinations in which each further fungicide B from the combinations 1 to 22 disclosed in table 1a is combined with each combination of the insecticides C1 and C2 from the combinations 42 to 46 disclosed in table 2b.

Examples of preferred quinternary combinations of kiralaxyl, three further fungicides B1, B2 and B3 and one insecticide C result when tables 3 and 1b are viewed together. These are quaternary combinations in which the combination of the further fungicides B1, B2 and B3 from the combination 47 disclosed in table 3 is combined with each insecticide C from the combinations 23 to 31 disclosed in table 1b.

Examples of preferred quinternary combinations of kiralaxyl, two further fungicides B1 and B2 and two insecticides C1 and C2 result when tables 2a and 2b are viewed together. These are quaternary combinations in which the combinations of the further fungicides B1 and B2 from the combinations 32 to 41 disclosed in table 2a are combined with each combination of the further insecticides C1 and C2 from the combinations 42 to 46 disclosed in table 2b.

Higher combinations of kiralaxyl and more than four further additional pesticides result when the tables mentioned above are viewed together.

The term "seed" is to be understood as meaning at least one seed and refers to a resting state which is physically separate from the vegetative state of a plant. Seed may be stored and/or used over a relatively long period of time to grow a further plant individuum of the same species from which the seed originates. The term "resting state" means that the viability remains in spite of the absence of light, water and/or nutrients essential for the vegetative state, i.e. the non-seed state.

According to the invention, seed treatment comprises allowing the active compounds to act on at least one seed. The method according to the invention can be used for a seed in any physiological state; however, it is preferred for the state of the seed to be stable enough so that it does not suffer any damage during treatment. Typically, the seed is a seed obtained on harvesting, removed from the plant or separated from the fruit or any other seed-carrying plant parts. Preferably, the biological stability of the seeds, too, is such that the seed does not suffer any biological damage during treatment. According to one embodiment, the treatment can be used for a seed which has been harvested, cleaned and dried to a moisture content of less than about 15% by weight. According to another embodiment, the seed to be treated may be a seed which has initially been dried and then primed with water and/or another material and which has then been dried again, before or during the treatment with the active compound combination according to the invention. In principle, the seed can be treated at any time between when it is obtained, i.e. in particular harvest, and sowing of the seed.

The treatment is expediently carried out using an unsown seed. The term "unsown seed" refers to a seed at any time between when it is obtained and the sowing of the seed in the soil, the latter for purposes of germination and growth of the plant.

Treatment of an unsown seed is not to be understood as meaning the procedures where the active compound combination is applied more to the soil than directly to the seed. By treating the seed prior to sowing the seed, the method is simplified. In this manner, seed can be treated, for example, at a central location and then distributed. This allows the handling of the active compound combination to be avoided when the seed is planted. It is just the treated seed which is planted in a manner customary for untreated seeds.

For treating the seed, it is possible, in principle, to use all customary methods of seed treatment or seed dressing. Specifically, the treatment is carried out by mixing the seed with the particular desired amount of active compound combination, in general in the form of one or more formulations, either as such or after prior dilution with water, in an apparatus suitable for this purpose, for example a mixing apparatus for solid or solid/liquid mixing partners, until the active compound combination is uniformly distributed on the seed. This procedure may comprise coating or drenching the seed with at least part of the active compound combination. Whereas on coating an active compound-comprising layer is formed on the surface of the seeds, on drenching at least part of the active compound combination penetrates into the inner part of the seeds. This is, if appropriate, followed by a drying step. Both procedures are familiar to the person skilled in the art.

Components A and B and/or C can be applied jointly or separately. In the case of separate use, the application of the individual active substances can be simultaneously or—as part of a treatment sequence—one after the other, where the application in the case of successive application is preferably carried out at an interval of from a few minutes to a number of days.

The amounts of active compounds (total amounts of active compounds) used are generally from 1 to 1000 g/100 kg of seed, preferably from 1 to 200 g/100 kg of seed, in particular from 5 to 100 g/100 kg of seed.

In a particular embodiment of the invention, the treatment protects not only the seed during storage and sowing and up to germination, but also the plants during germination and thereafter, preferably for longer than the emergence phase, particularly preferably for at least six weeks after sowing and again particularly preferably for at least four weeks after sowing.

According to the invention, the seed treatment protects against the phytopathogens mentioned above, in particular harmful fungi.

"Protection" is to be understood as meaning any measure or combination of measures which is suitable to reduce or completely prevent damage by foreign organisms. Here, "damage" includes any kind of qualitative and/or quantitative yield reduction (reduction of the number of germinating plants, the harvest yield, the fruit quality, etc.). Protection is to be considered as having been achieved when the damage of the treated seed and/or the plants grown therefrom is significantly reduced compared to that of the untreated seed and/or the plants grown therefrom.

The seed treatment is particularly suitable for protecting the following host plants against the following phytopathogenic fungi:

- vegetables, oilseed rape, sugarbeet, fruit or rice if the phytopathogen is an *Alternaria* species;
- corn or cereal if the phytopathogen is a *Drechslera* species,
- corn, soybeans, rice or sugarbeet if the phytopathogen is a *Cercospora* species,
- various host plants, in particular grasses, leguminous plants, peppers, oilseed rape, cucumbers, bananas or Solanaceae such as tomatoes, potatoes or eggplants, if the phytopathogen is a *Fusarium* species,
- various host plants, in particular grasses, leguminous plants, peppers, or Solanaceae such as tomatoes, potatoes or eggplants, if the phytopathogen is a *Verticillium* species,
- soybeans, vegetables or sorghum if the phytopathogen is a *Peronospora* or *Pseudoperonospora* species,
- sunflowers if the phytopathogen is a *Plasmopara* species,
- lawn grasses, rice, corn, cotton, oilseed rape, sunflowers, sugarbeet or vegetables if the phytopathogen is a *Pythium* species,
- cotton, rice, potatoes, lawn grasses, corn, oilseed rape, potatoes, sugarbeet or vegetables if the phytopathogen is a *Rhizoctonia* species,
- cereals if the phytopathogen is a *Tilletia* species, or
- cereals, corn or sugarbeet if the phytopathogen is an *Ustilago* species.

Surprisingly, the combinations according to the invention in which kiralaxyl is used together with the further fungicide(s) or insecticide(s) may have better fungicidal activity against harmful fungi than would have been expected based on the fungicidal activity of the individual compounds, i.e. the fungicidal activity is increased in a superadditive manner. This means that, by using kiralaxyl together with at least one further fungicide, an enhanced activity against harmful fungi in the sense of a synergetic effect (synergism) is achieved. For this reason, the combinations may be employed at lower total application rates. If kiralaxyl is combined with an insecticide, in addition to the fungicidal action, an insecticidal action is also obtained.

Accordingly, in a particular embodiment of the invention, dosages are used in which the individual pesticide components on their own do not necessarily already provide a protective action against the organism in question, but where this is achieved by the combination (synergism). In the case of combinations with more than two partners, the synergism may comprise all combination partners or only some of them, and it is also possible to combine in one combination partners which are synergistically effective with one another. Thus, ternary combinations may comprise two or three, quaternary combinations two, three or four or two times two, quinternary combinations two, three, four, five, two times two or two and three partners which are synergistically effective with one another. A group of partners is synergistic if at least one of them is present in a dose in which the partner on its own can not achieve a protective effect, but where this is the case in the presence of the partner(s), independently of whether the partner or the partners on its own or on their own may achieve a protective effect or not.

In a further particular embodiment of the invention, dosages are employed where each component on its own already achieves a protective effect against the organism in question, but where the activity spectra of the individual components differ from one another. Here, the actions of the individual components are particularly preferably complementary by acting independently of one another on harmful organisms which are frequently encountered together.

The compositions according to the invention include both compositions comprising kiralaxyl of the formula I and at least one further fungicide and/or one insecticide and kits comprising a first component which comprises kiralaxyl of the formula I and at least one further component which comprises at least one further fungicide and/or one insecticide, where the first and the further component are generally present in the form of separate formulations. These formulations can be applied simultaneously or at different times, as already mentioned for the methods according to the invention.

This applies correspondingly to the weight ratios of kits according to the invention, where said weight ratios may also be expressed in the form of instructions for use for the combined application of certain amounts of components A) and B) and/or C).

Depending on the embodiment in which the ready-to-use preparations of the compositions according to the invention are present, they comprise one or more liquid or solid carriers, if appropriate surfactants and if appropriate further auxiliaries customary for formulating fungicides and/or insecticides. The recipes for such formulations are familiar to the person skilled in the art.

Aqueous application forms can be prepared, for example, from emulsion concentrates, suspensions, pastes, wettable powders or water-dispersible granules by addition of water. To prepare emulsions, pastes or oil dispersions, the fungicides and/or insecticides, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, such concentrates being suitable for dilution with water.

The formulations are prepared in a known manner, for example by extending the fungicides and/or insecticides with solvents and/or carriers, if desired with the use of surfactants, i.e. emulsifiers and dispersants. Solvents/carriers suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, methyl hydroxybutyl ketone, diacetone alcohol, mesityl oxide, isophorone), lactones (for example gamma-butyrolactone), pyrrolidones (pyrrolidone, N-methylpyrrolidone, N-ethylpyrrolidone, n-octylpyrrolidone), acetates (glycol diacetate), glycols, dimethyl fatty acid amides, fatty acids and fatty acid esters. In principle, solvent mixtures may also be used.

Carriers such as ground natural minerals (for example kaolins, clays, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates), and dispersants such as lignosulfite waste liquors and methylcellulnse.

Suitable surfactants are alkali metal salts, alkaline earth metal salts and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenyl polyglycol ether, tributylphenyl polyglycol ether, tristerylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, mesityl oxide, isophorone, strongly polar solvents, for example dimethyl sulfoxide, 2-pyrrolidone, N-methylpyrrolidone, butyrolactone, or water.

Powders, compositions for broadcasting and dusts can be prepared by mixing or jointly grinding the active substances with a solid carrier.

Granules, for example coated granules, impregnated granules and homogeneous granules, can be prepared by binding the active compounds onto solid carriers. Solid carriers are, for example, mineral earths such as silica gels, silicates, talc, kaolin, attaclay, limestone, lime, chalk, bole, loess, clay, dolomite, diatomaceous earth (kieselguhr), calcium sulfate, magnesium sulfate, magnesium oxide, ground synthetic materials, fertilizers such as, for example, ammonium sulfate, ammonium phosphate, ammonium nitrate, ureas and plant products such as cereal meal, tree bark meal, wood meal and nutshell meal, cellulose powder and other solid carriers.

In general, the formulations comprise between 0.01 and 95% by weight, preferably between 0.1 and 90% by weight, in particular 5 to 50% by weight, of the fungicidally and/or insecticidally active compounds. In this context, the active compounds are employed in a purity of from 90% to 100%, preferably 95% to 100% (according to NMR spectrum).

Examples of Formulations are:

1. Products for Dilution in Water

I) Water-Soluble Concentrates (SL)

10% by weight of active compounds are dissolved in water or a water-soluble solvent. Alternatively, wetting agents or other adjuvants are added. Upon dilution in water, the active compound dissolves.

II) Dispersible Concentrates (DC)

20% by weight of active compounds are dissolved in cyclohexanone with addition of a dispersant, for example polyvinylpyrrolidone. Upon dilution in water, a dispersion results.

III) Emulsifiable Concentrates (EC)

15% by weight of active compounds are dissolved in xylene with addition of calcium dodecylbenzenesulfonate and castor oil ethoxylate (in each case 5%). Upon dilution in water, an emulsion results.

IV) Emulsions (EW, EO)

40% by weight of active compounds are dissolved in xylene with addition of calcium dodecylbenzenesulfonate and castor oil ethoxylate (in each case 5%). This mixture is introduced into water by means of an emulsifier (Ultraturrax) and made into a homogeneous emulsion. Upon dilution in water, an emulsion results.

V) Suspensions (SC, OD)

20% by weight of active compounds are comminuted in a stirred ball mill with addition of dispersants, wetting agents and water or an organic solvent to give a fine suspension of active compound. Upon dilution in water, a stable suspension of the active compound results.

VI) Water-Dispersible and Water-Soluble Granules (WG, SG)

50% by weight of active compounds are ground finely with addition of dispersants and wetting agents and made into water-dispersible or water-soluble granules by means of technical apparatuses (for example extrusion, spray tower, fluidized bed). Upon dilution in water, a stable dispersion or solution of the active compound results.

VII) Water-Dispersible and Water-Soluble Powders (WP, SP)

75% by weight of active compounds are ground in a rotor-stator mill with addition of dispersants, wetting agents and silica gel. Upon dilution in water, a stable dispersion or solution of the active compound results.

2. Products for Direct Application

VIII) Dusts (DP)

5% by weight of active compounds are ground finely and mixed intimately with 95% by weight of finely particulate kaolin. This gives a dust.

IX) Granules (GR, FG, GG, MG)

0.5% by weight of active compounds is ground finely and combined with 95.5% by weight of carriers. Current methods are extrusion, spray drying or the fluidized bed. This gives granules for direct application.

X) ULV Solutions (UL)

10% by weight of active compounds are dissolved in an organic solvent, for example xylene. This gives a product for direct application.

Particularly preferred formulations for treating seed are, for example:

I soluble concentrates (SL)
IV emulsions (EW, EO)
V suspensions (SC, OD)
VI water-dispersible and water-soluble granules (WG, SG)
VII water-dispersible and water-soluble powders (WP, SP)
VIII dusts and dust-like powders (DP)

Preferred solid compound formulations of the fungicides and/or insecticides for the treatment of seed usually comprise from 0.5 to 80% of active compound, from 0.05 to 5% of wetting agent, from 0.5 to 15% of dispersant, from 0.1 to 5% of thickener, from 5 to 20% of antifreeze agent, from 0.1 to 2% of antifoam, from 1 to 20% of pigment and/or dye, from 0 to 15% of tackifier or adhesive, from 0 to 75% of filler/vehicle, and from 0.01 to 1% of preservative.

Suitable pigments and/or dyes for formulations of the fungicides and/or insecticides for the treatment of seed are Pigment blue 15:4, Pigment blue 15:3, Pigment blue 15:2, Pigment blue 15:1, Pigment blue 80, Pigment yellow 1, Pigment yellow 13, Pigment red 112, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108.

Suitable wetting agents and dispersants are in particular the surfactants mentioned above. Preferred wetting agents are alkylnaphthalenesulfonates, such as diisopropyl- or diisobutylnaphthalenesulfonates. Preferred dispersants are nonionic or anionic dispersants or mixtures of nonionic or anionic dispersants. Suitable nonionic dispersants are in particular ethylene oxide/propylene oxide block copolymers, alkylphenol polyglycol ethers and also tristryrylphenol polyglycol ether, for example polyoxyethylene octylphenol ether, ethoxylated isooctylphenol, octylphenol, nonylphenol, alkylphenol polyglycol ethers, tributylphenyl polyglycol ether, tristerylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters and methylcellulose. Suitable anionic dispersants are in particular alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore arylsulfonate/formaldehyde condensates, for example condensates of sulfonated naphthalene and naphthalene derivatives with formaldehyde, condensates of naphthalene or of naphthalenesulfonic acid with phenol and formaldehyde, lignosulfonates, lignosulfite waste liquors, phosphated or sulfated derivatives of methylcellulose and polyacrylic acid salts.

Suitable for use as antifreeze agents are, in principle, all substances which lower the melting point of water. Suitable antifreeze agents include alkanols, such as methanol, ethanol, isopropanol, the butanols, glycol, glycerol, diethylene glycol and the like.

Suitable thickeners are all substances which can be used for such purposes in agrochemical compositions, for example cellulose derivatives, polyacrylic acid derivatives, xanthan, modified clays and finely divided silica.

Suitable for use as antifoams are all defoamers customary for formulating agrochemically active compounds. Particularly suitable are silicone antifoams and magnesium stearate.

Suitable for use as preservatives are all preservatives which can be employed for such purposes in agrochemical compositions. Dichlorophene, isothiazolenes, such as 1,2-benzisothiazol-3(2H)-one, 2-methyl-2H-isothiazol-3-one hydrochloride, 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one calcium chloride complex, 2-octyl-2H-isothiazol-3-one, and benzyl alcohol hemiformal may be mentioned by way of example.

Adhesives/tackifiers are added to improve the adhesion of the effective components on the seed after treatment. Suitable adhesives are EO/PO-based block copolymer surfactants, but also polyvinyl alcohols, polyvinylpyrrolidones, polyacrylates, polymethacrylates, polybutenes, polyisobutenes, polystyrene, polyethyleneamines, polyethyleneamides, polyethyleneimines (Lupasol®, Polymin®), polyethers and copolymers derived from these polymers.

Particular formulations for treating seed are seed coating formulations. In general, these comprise at least one special auxiliary which serves to form a suitable coating on the seeds. To this end, the abovementioned adhesives or tackifiers can be employed in combination with non-adhesive adsorbents. Appropriate adsorbents, such as the carrier materials described above, are familiar to the person skilled in the art.

EXAMPLES

The following examples serve the illustration of the invention only and are not to be interpreted as restricting the invention.

Example 1

Efficacy on Peas

Corus-type pea seed (*Pisum Sativum*) was treated in small-parcel field experiments in Great Britain with a mixture containing kiralaxyl, pyraclostrobin and triticonazole so that 10 g kiralaxyl, 10 g pyraclostrobin and 10 g triconazole were applied per 100 kg of seed. The number of plants that had emerged was determined eight weeks after sowing. The number of untreated plants that had emerged was defined as 100. The average relative number of plants that had emerged, determined on the basis of four repetitions with the seed treated with the mixture described above, was 175%.

Example 2

Efficacy on Corn

Anjou 290-type corn seed (*Zea mais*) was treated in small-parcel field experiments in France with a mixture containing kiralaxyl, pyraclostrobin and triticonazole so that 5 g kiralaxyl, 5 g pyraclostrobin and 5 g triticonazole were applied per 100 kg of seed. The height of the corn plants from four repetitions was determined four weeks after sowing. The height of the untreated plants was defined as 100. The average relative height of the corn plants from the seed treated with the mixture described above was 140%.

Example 3

Efficacy on Wheat

AC Domain-type spring wheat seed (*Triticum arvensis*) was treated in small-parcel field experiments in Canada with a mixture containing kiralaxyl, pyraclostrobin and triticonazole so that 5 g kiralaxyl, 5 g pyraclostrobin and 5 g triticonazole were applied per 100 kg of seed. The number of plants per meter of a row was determined one week after sowing. In the case of the untreated seed, an average of 10.9 wheat plants per row was ascertained. The average number of wheat plants in the case of the use of the seed treated with the mixture described above, determined on the basis of four repetitions, was 31.3

The invention claimed is:

1. A method for protecting a plant against a phytopathogen selected from the genera *Pythium, Rhizoctonia, Tilletia, Ustilago, Peronospora, Pseudoperonospora, Plasmopara, Alternaria, Cercospora, Drechslera, Fusarium* and *Verticillium,* wherein the seed of the plant is treated with

A) kiralaxyl of the formula I (I)

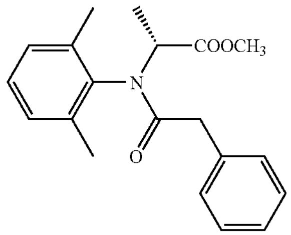

in synergistic combination with at least one further pesticide selected from

B) a further fungicide that is selected from the group consisting of pyraclostrobin, metconazole, prothioconazole, tebuconazole, penconazole, carboxin and fludioxonil or C) an insecticide consisting of fipronil.

2. The method according to claim 1 wherein protection against the following pathogens on the following plants is conferred:

the plant is selected from the group consisting of vegetables, oilseed rape, sugarbeet, fruit and rice if the phytopathogen is an *Alternaria* species;

the plant is selected from the group consisting of corn and cereal if the phytopathogen is a *Drechslera* species, the plant is selected from the group consisting of corn, soybeans, rice and sugarbeet if the phytopathogen is a *Cercospora* species, the plant is selected from the group consisting of grasses, leguminous plants, peppers, oilseed rape, cucumbers, bananas and Solanaceae such as tomatoes, potatoes and eggplants if the phytopathogen is a *Fusarium* species, the plant is selected from the group consisting of grasses, leguminous plants, peppers and Solanaceae such as tomatoes, potatoes and eggplants if the phytopathogen is a *Verticillium* species, the plant is selected from the group consisting of soybeans, vegetables and sorghum if the phytopathogen is a *Peronospora* or *Pseudoperonospora* species, the plant is selected from the group consisting of sunflowers if the phytopathogen is a *Plasmopara* species, the plant is selected from the group consisting of lawn grasses, rice, corn, cotton, oilseed rape, sunflowers, sugarbeet and vegetables if the phytopathogen is a *Pythium* species, the plant is selected from the group consisting of cotton, rice, potatoes, lawn grasses, corn, oilseed rape, sugarbeet and vegetables if the phytopathogen is a *Rhizoctonia* species, the plant is selected from the group consisting of cereal if the phytopathogen is a *Tilletia* species, or the plant is selected from the group consisting of cereal, corn and sugarbeet if the phytopathogen is an *Ustilago* species.

3. The method according to claim 1 wherein the kiralaxyl of formula I is combined with a further fungicide that is selected from the group consisting of pyraclostrobin, metconazole, prothioconazole, tebuconazole, penconazole, carboxin and fludioxonil.

4. The method according to claim 1 wherein the kiralaxyl of formula I is combined with the insecticide fipronil.

5. The method according to claim 1 wherein kiralaxyl and the further pesticide are applied simultaneously or in succession.

6. A composition for treating seed of a plant for protecting the plant against a phytopathogen selected from the genera *Pythium, Rhizoctonia, Tilletia, Ustilago, Peronospora, Pseudoperonospora, Plasmopara, Alternaria, Cercospora, Drechslera, Fusarium* and *Verticillium*, the composition comprising:

A) kiralaxyl of the formula I (I)

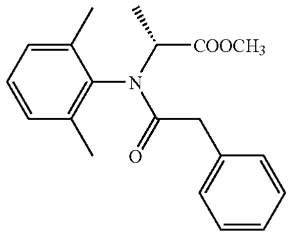

in synergistic combination with at least one further pesticide selected from

B) a further fungicide that is selected from the group consisting of pyraclostrobin, metconazole, prothioconazole, tebuconazole, penconazole, carboxin, and fludioxonil;

C) an insecticide consisting of fipronil.

7. The composition according to claim 6 in the form of a composition comprising kiralaxyl of the formula I and the further pesticide.

8. The composition according to claim 6 in the form of a kit comprising a first component comprising kiralaxyl of the formula I and at least one further component comprising the further pesticide.

9. The composition according to claim 6 comprising kiralaxyl of the formula I and a further fungicide that is selected from the group consisting of pyraclostrobin, metconazole, prothioconazole, tebuconazole, penconazole, carboxin and fludioxonil.

10. The composition according to claim 6 comprising kiralaxyl of the formula I and an insecticide consisting of fipronil.

* * * * *